(12) United States Patent
McHale et al.

(10) Patent No.: US 11,179,185 B2
(45) Date of Patent: Nov. 23, 2021

(54) CRYOGENIC SURGICAL SYSTEMS

(71) Applicant: AtriCure, Inc., Mason, OH (US)

(72) Inventors: Jonathon McHale, Cincinnati, OH (US); Frank M. Fago, Mason, OH (US); Stefan Stefanov, Ludlow, KY (US)

(73) Assignee: AtriCure, Inc., Mason, OH (US)

( * ) Notice: Subject to any disclaimer, the term of this patent is extended or adjusted under 35 U.S.C. 154(b) by 346 days.

(21) Appl. No.: 16/515,233

(22) Filed: Jul. 18, 2019

(65) Prior Publication Data

US 2020/0022745 A1 Jan. 23, 2020

Related U.S. Application Data

(60) Provisional application No. 62/701,384, filed on Jul. 20, 2018.

(51) Int. Cl.
*A61B 18/02* (2006.01)
*A61B 18/00* (2006.01)
*A61B 17/00* (2006.01)

(52) U.S. Cl.
CPC .... *A61B 18/02* (2013.01); *A61B 2017/00199* (2013.01); *A61B 2018/00672* (2013.01); *A61B 2018/00678* (2013.01); *A61B 2018/00714* (2013.01); *A61B 2018/00744* (2013.01); *A61B 2018/00791* (2013.01); *A61B 2018/0262* (2013.01)

(58) Field of Classification Search
CPC .......................... A61B 18/02; A61B 2018/0262
See application file for complete search history.

(56) References Cited

U.S. PATENT DOCUMENTS

| | | |
|---|---|---|
| 3,161,050 A | 12/1964 | Exner |
| 4,831,846 A | 5/1989 | Sungaila |
| 4,946,460 A | 8/1990 | Merry et al. |
| 5,465,583 A | 11/1995 | Goode |
| 7,114,390 B2 | 10/2006 | Lizon et al. |
| 9,801,676 B2 | 10/2017 | George et al. |
| 2005/0081541 A1 | 4/2005 | Copping |
| 2009/0281533 A1 | 11/2009 | Ingle et al. |
| 2010/0042087 A1* | 2/2010 | Goldboss .......... A61B 18/0218 606/22 |

(Continued)

FOREIGN PATENT DOCUMENTS

AU 2004200764 A1 10/2004

OTHER PUBLICATIONS

Atricure, Inc., cryoICE BOX—V6 Brochure, PDF file dated Sep. 5, 2017.

(Continued)

*Primary Examiner* — Daniel W Fowler
(74) *Attorney, Agent, or Firm* — Dorton & Willis, LLP; Ryan Willis

(57) ABSTRACT

Medical devices and related methods, and, more specifically, cryogenic surgical systems and related methods are disclosed. Some example cryogenic surgical systems may include a cryosurgical control unit configured to cool a cryosurgical probe to a temperature colder than a temperature at which flow of cryogenic fluid to the probe is stopped. Some example tank level indicating systems may utilize the pressure of the fluid in the tank and a temperature of the exterior wall of the tank to indicate liquid level.

14 Claims, 4 Drawing Sheets

(56) References Cited

U.S. PATENT DOCUMENTS

| | | | |
|---|---|---|---|
| 2010/0049184 A1* | 2/2010 | George | A61B 18/02 606/21 |
| 2010/0179527 A1 | 7/2010 | Watson et al. | |
| 2010/0241371 A1 | 9/2010 | Ammouri et al. | |
| 2014/0163538 A1* | 6/2014 | Ryba | A61F 7/0085 606/21 |
| 2014/0276698 A1* | 9/2014 | Wittenberger | A61B 18/02 606/21 |
| 2016/0008049 A1* | 1/2016 | Mahrouche | A61B 18/02 606/21 |
| 2019/0029745 A1* | 1/2019 | O'Connor | A61B 18/0218 |

OTHER PUBLICATIONS

Atricure, Inc., cryoICE BOX—V6 User's Manual, PDF file dated Jun. 21, 2017.

Atricure, Inc., cryoICE Cryoblation System Brochure, PDF file dated Mar. 11, 2019.

Atricure, Inc., cryoICE cryo-ablation probe Instructions for Use, PDF file dated Nov. 7, 2017.

Patent Cooperation Treaty, Search Report with Written Opinion and Search History, WIPO PCT Patent Application PCT/US2019/042329, dated Nov. 19, 2019.

* cited by examiner

CRYOGENIC SURGICAL SYSTEMS

CROSS REFERENCE TO RELATED APPLICATIONS

This application claims the benefit of U.S. Provisional Application No. 62/701,384, filed Jul. 20, 2018, which is incorporated by reference.

INTRODUCTION TO THE INVENTION

The present disclosure is directed to medical devices and related methods, and, more specifically, to cryogenic surgical systems and related methods.

The present disclosure contemplates that an amount of a fluid being in a mixed phase within a tank may be estimated by subtracting the weight of the empty tank from the weight of the tank and its contents. This approach, however, may not be accurate particularly if the noted weight of the tank is inaccurate and/or if the scale is defective. In order to overcome potential uncertainties about empty tank weight and a weight scale being defective, the present disclosure contemplates determining the amount of liquid within a container, regardless of the container's weight and without using a weight scale. Rather, the instant disclosure provides a method and apparatus for ascertaining an amount of cryogenic fluid within a tank knowing the fluid contained therein, the pressure of the fluid inside the container, and the temperature of the tank and/or fluid within the tank. In this manner, the instant disclosure provides a novel improvement upon the prior art in determining how much of a liquid is within a tank but avoiding having to know either the weight of the tank or its contents.

It is a first aspect of the present disclosure to provide a cryogenic surgical system, comprising: (a) a cryosurgical probe fluidically interposing an inlet conduit arranged to supply a cryogenic fluid to the cryosurgical probe and an exhaust conduit arranged to direct the cryogenic fluid away from the cryosurgical probe; and (b) a cryosurgical control unit capable of receiving the cryogenic fluid from a cryogenic fluid source, the cryosurgical control unit comprising an inlet valve fluidically coupled to the inlet conduit and configured to selectively supply the cryogenic fluid to the cryosurgical probe via the inlet conduit and an exhaust valve fluidically coupled to the exhaust conduit and configured to selectively permit cryogenic fluid to flow from the exhaust conduit, where the cryosurgical control unit is configured to control cooling of the cryosurgical probe to a temperature lower than a first setpoint temperature by (1) cooling the cryosurgical probe by opening the inlet valve to supply the cryogenic fluid to the cryosurgical probe, (2) shutting the inlet valve when a temperature of the cryosurgical probe reaches the first setpoint temperature, (3) maintaining the inlet valve shut while the cryosurgical probe temperature is less than the first setpoint temperature.

In a more detailed embodiment of the first aspect, the cryosurgical control unit is configured to open the inlet valve to supply the cryogenic fluid to the cryosurgical probe when the temperature of the cryosurgical probe reaches a second setpoint temperature, after maintaining the inlet valve shut while the cryosurgical probe temperature is less than the first setpoint temperature. In yet another more detailed embodiment, the second setpoint temperature is higher than the first setpoint temperature. In a further detailed embodiment, the cryosurgical control unit is configured to control cooling of the cryosurgical probe to a temperature less than the first setpoint temperature by (1) cooling the cryosurgical probe by opening the inlet valve to supply the cryogenic fluid to the cryosurgical probe and opening the exhaust valve to permit the cryogenic fluid to exhaust from the cryogenic probe, (2) shutting the inlet valve and maintaining the exhaust valve open when the temperature of the cryosurgical probe reaches the first setpoint temperature, (3) maintaining the inlet valve shut and maintaining the exhaust valve open while the cryosurgical probe temperature is less than the first setpoint temperature. In still a further detailed embodiment, the cryosurgical control unit is configured to receive the cryogenic fluid as a gas, and the cryosurgical probe includes an orifice capable of liquefying at least a portion of the gas. In a more detailed embodiment, the cryosurgical fluid comprises at least one of gaseous nitrous oxide and gaseous carbon dioxide.

It is a second aspect of the present disclosure to provide a method of operating a cryosurgical probe, the method comprising: (a) cooling the cryosurgical probe to a first setpoint temperature by supplying a cryogenic fluid to the cryosurgical probe via an inlet valve; (b) shutting the inlet valve when a temperature of the cryosurgical probe reaches the first setpoint temperature; and (c) cooling the cryosurgical probe to a temperature lower than the first setpoint temperature while the inlet valve remains shut.

In a more detailed embodiment of the second aspect, the method further includes, after cooling the cryosurgical probe to the temperature lower than the first setpoint temperature, opening the inlet valve when the temperature of the cryosurgical probe reaches a second setpoint temperature. In yet another more detailed embodiment, the second setpoint temperature is higher than the first setpoint temperature. In a further detailed embodiment, cooling the cryosurgical probe to the first setpoint temperature includes exhausting the cryogenic fluid from the cryosurgical probe via an exhaust valve, and a position of the exhaust valve is not changed during cooling the cryosurgical probe to the first setpoint temperature operation, the shutting the inlet valve operation, and cooling the cryosurgical probe to the temperature less than the first setpoint temperature operation. In still a further detailed embodiment, cooling the cryosurgical probe to the first setpoint temperature comprises operating the cryosurgical probe at a first back pressure, and cooling the cryosurgical probe to the temperature less than the first setpoint temperature comprises operating the cryosurgical probe at a second back pressure, the second back pressure being lower than the first back pressure. In a more detailed embodiment, an exhaust flow path for cryogenic fluid leaving the cryosurgical probe is substantially the same in cooling the cryosurgical probe to the first setpoint temperature operation and cooling the cryosurgical probe to the temperature less than the first setpoint temperature operation. In a more detailed embodiment, the cryosurgical fluid is supplied to the cryosurgical probe as a gas, and cooling the cryosurgical probe to the first setpoint temperature operation comprises liquefying at least a portion of the gas by flowing the gaseous cryogenic fluid through an orifice. In another more detailed embodiment, the cryosurgical fluid comprises at least one of gaseous nitrous oxide and gaseous carbon dioxide.

It is a third aspect of the present disclosure to provide a system configured to display an indicium associated with a liquid level in a tank, the tank containing liquid and gas phases of a fluid, the system comprising: (a) a heater thermally coupled to an exterior wall of the tank; (b) a pressure sensor arranged to measure a pressure of the fluid in the tank; (c) a temperature sensor arranged to measure a temperature of the exterior wall of the tank; and (d) an indicator capable of displaying an indicium associated with a first discrete liquid level, an indicium associated with a second discrete liquid level, and an indicium associated with a third discrete liquid level, the first discrete liquid level corresponding to a relatively higher liquid level in the tank, the second discrete liquid level corresponding to an intermediate liquid level in the tank, and the third discrete liquid level corresponding to a relatively lower liquid level in the tank, where the indicator displays one of the indicium associated with the first discrete liquid level, the indicium associated with the second discrete liquid level, and the indicium associated with the third discrete liquid level by determining, in sequence, which of the following sets of criteria is satisfied and, upon determining that a particular set of criteria is satisfied, displaying the indicium associated with the liquid level in the tank that is associated with that particular set of criteria: (I) displaying an indicium associated with a first discrete liquid level if (A) (1) the pressure of the fluid in the tank is greater than a first threshold pressure and (2) the temperature of the exterior wall is less than a first threshold temperature; (II) displaying an indicium associated with a second discrete liquid level if (A) (1) the pressure of the fluid in the tank is the pressure of the fluid in the tank is greater than a second threshold pressure and (2) the temperature of the exterior wall is less than a second threshold temperature; and (III) displaying an indicium associated with a third discrete liquid level if (A) (1) the pressure of the fluid in the tank is less than a third threshold pressure and (2) the temperature of the exterior wall is greater than a third threshold temperature.

In a more detailed embodiment of the third aspect, where set of criteria (I) comprises (I) displaying the indicium associated with the first discrete liquid level if (A) (1) the immediately previously displayed indicium was the indicium associated with the first discrete liquid level, (2) the pressure of the fluid in the tank is greater than a first threshold pressure, and (3) the temperature of the exterior wall is less than a first threshold temperature; where set of criterial (II) comprises (II) displaying the indicium associated with the second discrete liquid level if (A) (1) the immediately previously displayed indicium was the indicium associated with the first discrete liquid level, (2) at least one of (a) the pressure of the fluid in the tank is less than the first threshold pressure and (b) the temperature of the exterior wall is greater than the first threshold temperature and (3) the pressure of the fluid in the tank is greater than a second threshold pressure and the temperature of the exterior wall is less than a second threshold temperature, or (B) (1) the immediately previously displayed indicium was the indicium associated with the second discrete liquid level, (2) the pressure of the fluid in the tank is greater than the second threshold pressure, and (3) the temperature of the exterior wall is less than the second threshold temperature; and, where set of criterial (III) comprises (III) displaying the indicium associated with the third discrete liquid level if (A) (1) the immediately previously displayed indicium was the indicium associated with the first discrete liquid level, (2) at least one of (a) the pressure of the fluid in the tank is less than the first threshold pressure and (b) the temperature of the exterior wall is greater than the first threshold temperature, (3) at least one of (a) the pressure of the fluid in the tank is less than the second threshold pressure and (b) the temperature of the exterior wall is greater than the second threshold temperature, and (4) (a) the pressure of the fluid in the tank is less than a third threshold pressure and (b) the temperature of the exterior wall is greater than a third threshold temperature, or (B) (1) the immediately previously displayed indicium was the indicium associated with the second discrete liquid level, (2) at least one of (a) the pressure of the fluid in the tank is less than the second threshold pressure and (b) the temperature of the exterior wall is greater than the second threshold temperature, and (2) (a) the pressure of the fluid in the tank is less than the third threshold pressure and (b) the temperature of the exterior wall is greater than the third threshold temperature, or (C) (1) the immediately previously displayed indicium was the indicium associated with the third discrete liquid level, (2) the pressure of the fluid in the tank is less than the third threshold pressure, and (3) the temperature of the exterior wall is greater than the third threshold temperature.

In yet another more detailed embodiment of the third aspect, the first threshold pressure and the second threshold pressure are substantially the same. In yet another more detailed embodiment, the third threshold pressure is higher than at least one of the first threshold pressure and the second threshold pressure. In a further detailed embodiment, the first threshold temperature is lower than the second threshold temperature. In still a further detailed embodiment, the third threshold temperature is higher than the first threshold temperature and the second threshold temperature. In a more detailed embodiment, the heater comprises a heater band removably disposed at least partially around the exterior wall of the tank. In a more detailed embodiment, the temperature sensor is disposed on the heater band. In another more detailed embodiment, the heater band is disposed on a lower portion of the exterior wall of the tank and the temperature sensor is disposed proximate an upper end of the heater band. In yet another more detailed embodiment, the heater band is capable of varying a heat output of the heater band to maintain the pressure of the fluid in the tank within a pressure setpoint range. In still another more detailed embodiment, the fluid comprises at least one of nitrous oxide and carbon dioxide.

It is a fourth aspect of the present disclosure to provide a method of indicating a liquid level in a tank, the method comprising: (a) heating a tank using a heater thermally coupled to an exterior wall of the tank, the tank being pressurized and containing liquid and gas phases of a fluid; (b) measuring a pressure of the fluid in the tank; (c) measuring a temperature of the exterior wall of the tank; and (d) displaying an indicium associated with a liquid level in the tank by (I) displaying an indicium associated with a first discrete liquid level if (A) (1) the pressure of the fluid in the tank is greater than a first threshold pressure and (2) the temperature of the exterior wall is less than a first threshold temperature; (II) displaying an indicium associated with a second discrete liquid level if (A) (1) the pressure of the fluid in the tank is greater than a second threshold pressure and (2) the temperature of the exterior wall is less than a second threshold temperature; and (III) displaying an indicium associated with a third discrete liquid level if (A) (1) the pressure of the fluid in the tank is less than a third threshold pressure and (2) the temperature of the exterior wall is greater than a third threshold temperature, where the indicium associated with the first discrete liquid level corresponds to a relatively higher level of liquid in the tank, the indicium associated with the second discrete liquid level corresponds to an intermediate level of liquid in the tank, and the indicium associated with the third discrete liquid level corresponds to a relatively lower level of liquid in the tank.

It is a fifth aspect of the present disclosure to provide a method of indicating a liquid level in a tank, the method comprising: (a) heating a tank using a heater thermally coupled to an exterior wall of the tank, the tank being pressurized and containing liquid and gas phases of a fluid; (b) measuring a pressure of the fluid in the tank; (c) measuring a temperature of the exterior wall of the tank; and (d) displaying an indicium associated with a liquid level in the tank by determining whether an immediately previously displayed indicium was an indicium associated with the first discrete liquid level, an indicium associated with the second discrete liquid level, or an indicium associated with the third discrete liquid level, and (I) displaying the indicium associated with the first discrete liquid level if (A) (1) the immediately previously displayed indicium was the indicium associated with the first discrete liquid level, (2) the pressure of the fluid in the tank is greater than a first threshold pressure, and (3) the temperature of the exterior wall is less than a first threshold temperature; (II) displaying the indicium associated with the second discrete liquid level if (A) (1) the immediately previously displayed indicium was the indicium associated with the first discrete liquid level, (2) at least one of (a) the pressure of the fluid in the tank is less than the first threshold pressure and (b) the temperature of the exterior wall is greater than the first threshold temperature and (3) the pressure of the fluid in the tank is greater than a second threshold pressure and the temperature of the exterior wall is less than a second threshold temperature, or (B) (1) the immediately previously displayed indicium was the indicium associated with the second discrete liquid level, (2) the pressure of the fluid in the tank is greater than the second threshold pressure, and (3) the temperature of the exterior wall is less than the second threshold temperature; and (III) displaying the indicium associated with the third discrete liquid level if (A) (1) the immediately previously displayed indicium was the indicium associated with the first discrete liquid level, (2) at least one of (a) the pressure of the fluid in the tank is less than the first threshold pressure and (b) the temperature of the exterior wall is greater than the first threshold temperature, (3) at least one of (a) the pressure of the fluid in the tank is less than the second threshold pressure and (b) the temperature of the exterior wall is greater than the second threshold temperature, and (4) (a) the pressure of the fluid in the tank is less than a third threshold pressure and (b) the temperature of the exterior wall is greater than a third threshold temperature, or (B) (1) the immediately previously displayed indicium was the indicium associated with the second discrete liquid level, (2) at least one of (a) the pressure of the fluid in the tank is less than the second threshold pressure and (b) the temperature of the exterior wall is greater than the second threshold temperature, and (2) (a) the pressure of the fluid in the tank is less than the third threshold pressure and (b) the temperature of the exterior wall is greater than the third threshold temperature, or (C) (1) the immediately previously displayed indicium was the indicium associated with the third discrete liquid level, (2) the pressure of the fluid in the tank is less than the third threshold pressure, and (3) the temperature of the exterior wall is greater than the third threshold temperature, where the indicium associated with the first discrete liquid level corresponds to a relatively higher level of liquid in the tank, the indicium associated with the second discrete liquid level corresponds to an intermediate level of liquid in the tank, and the indicium associated with the third discrete liquid level corresponds to a relatively lower level of liquid in the tank.

It is a sixth aspect of the present disclosure to provide a method of indicating a liquid level in a tank, the method comprising: (a) heating a tank using a heater thermally coupled to an exterior wall of the tank, the tank being pressurized and containing liquid and gas phases of a fluid; (b) measuring a pressure of the fluid in the tank; (c) measuring a temperature of the exterior wall of the tank; and (d) displaying an indicium associated with a liquid level in the tank by determining, in sequence, which of the following sets of criteria is satisfied and, upon determining that a particular set of criteria is satisfied, displaying the indicium associated with the liquid level in the tank that is associated with that particular set of criteria: (I) displaying an indicium associated with a first discrete liquid level if (A) (1) the pressure of the fluid in the tank is greater than a first threshold pressure and (2) the temperature of the exterior wall is less than a first threshold temperature; (II) displaying an indicium associated with a second discrete liquid level if (A) (1) the pressure of the fluid in the tank is the pressure of the fluid in the tank is greater than a second threshold pressure and (2) the temperature of the exterior wall is less than a second threshold temperature; and (III) displaying an indicium associated with a third discrete liquid level if (A) (1) the pressure of the fluid in the tank is less than a third threshold pressure and (2) the temperature of the exterior wall is greater than a third threshold temperature, where the indicium associated with the first discrete liquid level corresponds to a relatively higher level of liquid in the tank, the indicium associated with the second discrete liquid level corresponds to an intermediate level of liquid in the tank, and the indicium associated with the third discrete liquid level corresponds to a relatively lower level of liquid in the tank.

In yet another more detailed embodiment of the sixth aspect, displaying the indicium associated with a liquid level in the tank includes displaying the indicium associated with the liquid level in the tank by determining whether an immediately previously displayed indicium was the indicium associated with the first discrete liquid level, the indicium associated with the second discrete liquid level, or the indicium associated with the third discrete liquid level, and by determining, in sequence, which of the following sets of criteria is satisfied and, upon determining that the particular set of criteria is satisfied, displaying the indicium associated with the liquid level in the tank that is associated with that particular set of criteria: (I) displaying the indicium associated with the first discrete liquid level if (A) (1) the immediately previously displayed indicium was the indicium associated with the first discrete liquid level, (2) the pressure of the fluid in the tank is greater than a first threshold pressure, and (3) the temperature of the exterior wall is less than a first threshold temperature; (II) displaying the indicium associated with the second discrete liquid level if (A) (1) the immediately previously displayed indicium was the indicium associated with the first discrete liquid level, (2) at least one of (a) the pressure of the fluid in the tank is less than the first threshold pressure and (b) the temperature of the exterior wall is greater than the first threshold temperature and (3) the pressure of the fluid in the tank is greater than a second threshold pressure and the temperature of the exterior wall is less than a second threshold temperature, or (B) (1) the immediately previously displayed indicium was the indicium associated with the second discrete liquid level, (2) the pressure of the fluid in the tank is greater than the second threshold pressure, and (3) the temperature of the exterior wall is less than the second threshold temperature; and (III) displaying the indicium associated with the third discrete liquid level if (A) (1) the immediately previously displayed indicium was the indicium associated with the first discrete liquid level, (2) at least one of (a) the pressure of the fluid in the tank is less than the first threshold pressure and (b) the temperature of the exterior wall is greater than the first threshold temperature, (3) at least one of (a) the pressure of the fluid in the tank is less than the second threshold pressure and (b) the temperature of the exterior wall is greater than the second threshold temperature, and (4) (a) the pressure of the fluid in the tank is less than a third threshold pressure and (b) the temperature of the exterior wall is greater than a third threshold temperature, or (B) (1) the immediately previously displayed indicium was the indicium associated with the second discrete liquid level, (2) at least one of (a) the pressure of the fluid in the tank is less than the second threshold pressure and (b) the temperature of the exterior wall is greater than the second threshold temperature, and (2) (a) the pressure of the fluid in the tank is less than the third threshold pressure and (b) the temperature of the exterior wall is greater than the third threshold temperature, or (C) (1) the immediately previously displayed indicium was the indicium associated with the third discrete liquid level, (2) the pressure of the fluid in the tank is less than the third threshold pressure, and (3) the temperature of the exterior wall is greater than the third threshold temperature.

In yet another more detailed embodiment, the method further includes before the displaying the indicium associated with the liquid level operation, if the tank is a full replacement tank, considering the immediately previously displayed indicium to be the indicium associated with the first discrete liquid level. In a further detailed embodiment, the first threshold pressure and the second threshold pressure are substantially the same. In still a further detailed embodiment, the third threshold pressure is higher than at least one of the first threshold pressure and the second threshold pressure. In a more detailed embodiment, the third threshold temperature is higher than the first threshold temperature and the second threshold temperature. In a more detailed embodiment, at least one of the indicium associated with the first discrete liquid level, the indicium associated with the second discrete liquid level, and the indicium associated with the third discrete liquid level comprises at least one of an audible indication, a visual indication, and a tactile indication. In another more detailed embodiment, heating the tank using the heater comprises heating the tank using a heater band removably disposed at least partially around the exterior wall of the tank. In yet another more detailed embodiment, measuring the temperature of the exterior wall of the tank comprises sensing the temperature of the exterior wall of the tank using a temperature sensor disposed on the heater band. In still another more detailed embodiment, heating the tank using the heater band comprises removably installing the heater band about a lower portion of the exterior wall of the tank, the temperature sensor being disposed proximate an upper end of the heater band.

In yet another more detailed embodiment, heating the tank using the heater band comprises varying a heat output of the heater band to maintain the pressure of the fluid in the tank within a pressure setpoint range. In a further detailed embodiment, varying the heat output of the heater band comprises cycling electrical power to the heater band on and off.

It is a seventh aspect of the present disclosure to provide a liquid level determination apparatus comprising: (a) a visual display configured to display an indicium indicative of a liquid level within a tank; (b) a processor communicatively coupled to the display; (c) a memory communicatively coupled to the processor, the memory containing instructions that, when executed by the processor, cause the apparatus to display, on the visual display, the indicium associated with the liquid level in the tank by determining, in sequence, which of the following sets of criteria is satisfied and, upon determining that a particular set of criteria is satisfied, displaying the indicium associated with the liquid level in the tank that is associated with that particular set of criteria: (I) displaying a first indicium associated with a first discrete liquid level if (A) (1) the pressure of the fluid in the tank is greater than a first threshold pressure and (2) the temperature of the exterior wall is less than a first threshold temperature; (II) displaying a second indicium associated with a second discrete liquid level if (A) (1) the pressure of the fluid in the tank is the pressure of the fluid in the tank is greater than a second threshold pressure and (2) the temperature of the exterior wall is less than a second threshold temperature; and (III) displaying a third indicium associated with a third discrete liquid level if (A) (1) the pressure of the fluid in the tank is less than a third threshold pressure and (2) the temperature of the exterior wall is greater than a third threshold temperature, where the first indicium corresponds to a relatively higher level of liquid in the tank, the second indicium corresponds to an intermediate level of liquid in the tank, and the third indicium corresponds to a relatively lower level of liquid in the tank.

BRIEF DESCRIPTION OF THE DRAWINGS

Example embodiments are described in conjunction with the accompanying drawing figures in which.

DETAILED DESCRIPTION

Example embodiments according to the present disclosure are described and illustrated below to encompass devices, methods, and techniques relating to medical procedures. Of course, it will be apparent to those of ordinary skill in the art that the embodiments discussed below are examples and may be reconfigured without departing from the scope and spirit of the present disclosure. It is also to be understood that variations of the example embodiments contemplated by one of ordinary skill in the art shall concurrently comprise part of the instant disclosure. However, for clarity and precision, the example embodiments as discussed below may include optional steps, methods, and features that one of ordinary skill should recognize as not being a requisite to fall within the scope of the present disclosure.

The present disclosure includes, inter alia, medical devices and related methods, and, more specifically, cryogenic surgical systems and related methods. The present disclosure contemplates that some cryogenic surgical systems, such as those utilizing certain cryogenic fluids and/or some cryosurgical probes incorporating small diameter inlet and exhaust conduits, may have a limited ability to cool the cryosurgical probes as much as may be desirable for some surgical procedures. Accordingly, the present disclosure contemplates that it may be beneficial to provide improved techniques and/or apparatus that facilitate enhanced cooling of cryosurgical probes. Additionally, the present disclosure contemplates that it may be beneficial to provide improved techniques and/or apparatus associated with indicating the liquid level in tanks utilized for cryogenic fluids in connection with cryogenic surgical systems.

Figure 1:
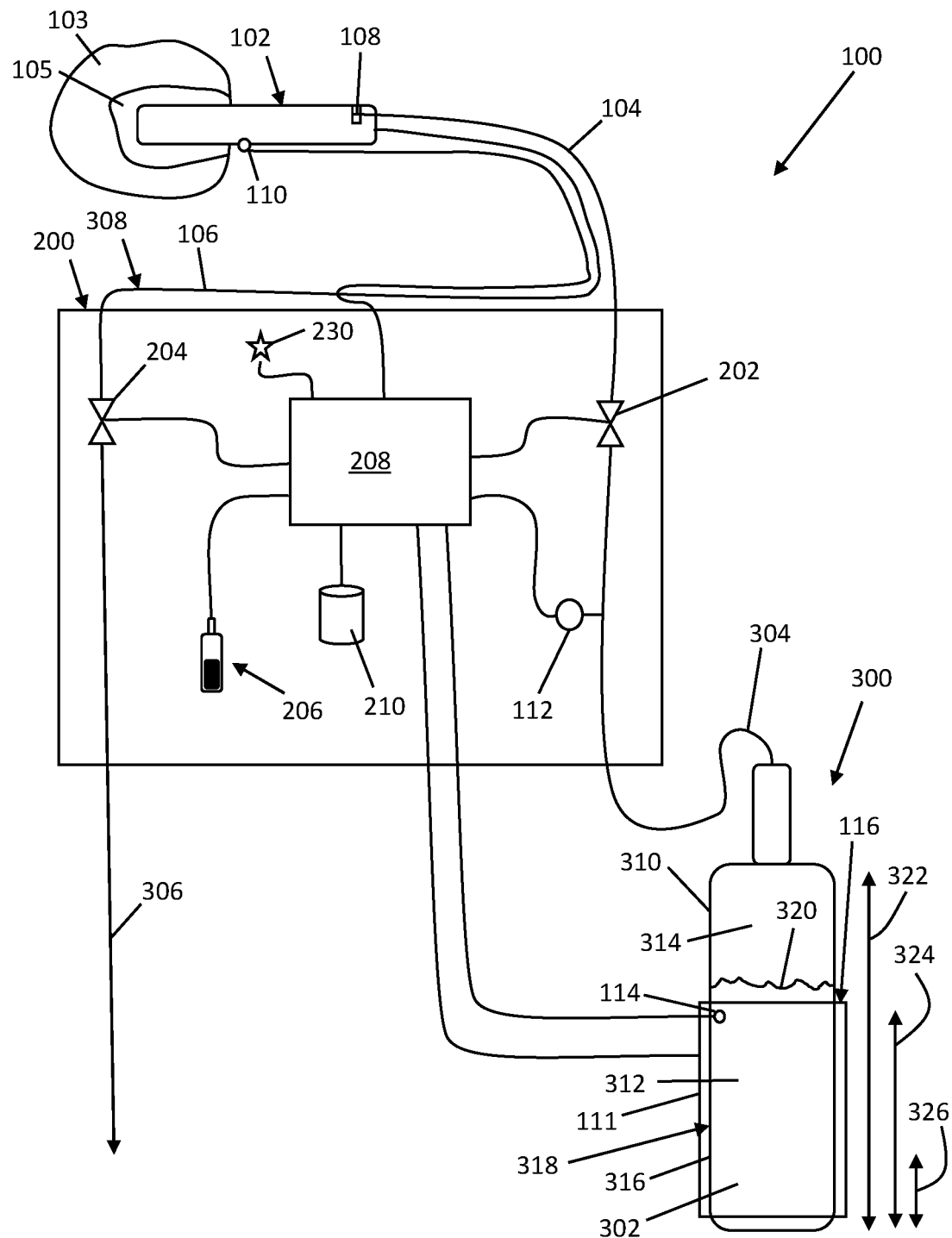
FIG. 1 is a schematic diagram of an example cryogenic surgical system.

FIG. 1 is a schematic diagram of an example cryogenic surgical system 100, according to at least some aspects of the present disclosure. System 100 may include a cryosurgical probe 102 and/or a cryosurgical control unit 200, which may be coupled to a cryogenic fluid source 300 containing a cryogenic fluid 302.

Generally, the cryosurgical control unit 200 may be configured to control cooling and/or heating (e.g., defrosting) of the cryosurgical probe 102, such as by controlling the flow of cryogenic fluid 302 to and/or from the cryosurgical probe 102. In some example embodiments, and with the exception of the improvements described in the present disclosure, the illustrative cryosurgical control unit 200 of the cryogenic surgical system 100 may be generally similar to the "cryoICE BOX" cryogenic surgical units available from AtriCure, Inc. of Mason, Ohio.

The cryogenic surgical system 100 may be configured to cool cryosurgical probe 102 so that it may have a desired cryosurgical effect (e.g., ablation, cryoanalgesia, etc.) on a target tissue 103. In some example applications, cryosurgical probe 102 may form an ice ball 105 in, on, and/or around the target tissue 103. Some example cryosurgical probes that may be suitable for use with the illustrative cryosurgical system 100 may include the "cryoICE," "cryoFORM," and/or "cryoSPHERE" probes available from AtriCure, Inc. of Mason, Ohio.

The cryosurgical probe 102 may be fluidically coupled to an inlet conduit 104, which may be arranged to supply cryogenic fluid 302 from the cryogenic control unit 200 to the cryosurgical probe 102. Similarly, the cryosurgical probe 102 may be fluidically coupled to an exhaust conduit 106, which may be arranged to convey cryogenic fluid 302 from the cryosurgical probe 102 to the cryosurgical control unit 200. Accordingly, cryogenic fluid 302 may flow through the inlet conduit 104, through the cryosurgical probe 102, and through the exhaust conduit 106, so that the cryosurgical probe fluidically interposes the inlet conduit 104 and the exhaust conduit 106. In some example embodiments, the cryosurgical probe 102 may include an orifice 108 fluidically interposing the inlet conduit 104 and the exhaust conduit 106. The orifice 108 may be configured to liquefy at least portion of a gaseous cryogenic fluid 302 flowing through the cryosurgical probe 102, such as by the Joule-Thomson effect. In some example embodiments, the cryosurgical probe 102 may include a temperature sensor 110, such as a thermocouple, which may be configured to measure a temperature of the cryosurgical probe 102.

The cryosurgical control unit 200 may be configured to receive cryogenic fluid 302 from the cryogenic fluid source 300, such as via a cryogenic fluid supply line 304. The cryosurgical control unit 200 may include an inlet valve 202 fluidically coupled between the cryogenic fluid supply line 304 extending from the cryogenic fluid source 300 and the inlet conduit 104 extending to the cryosurgical probe 102. The inlet valve 202 may be configured to selectively supply cryogenic fluid 302 to the cryosurgical probe 102 via the inlet conduit 104. The cryosurgical control unit 200 may include an exhaust valve 204 fluidically coupled between the exhaust conduit 106 extending from the cryosurgical probe 102 and an exhaust hose 306, which may be configured to direct exhausted cryogenic fluid 302 to an appropriate location. The exhaust valve 204 may be configured to selectively permit cryogenic fluid 302 to flow from the exhaust conduit 106 to the exhaust hose 306. Collectively, the exhaust conduit 106, the exhaust valve 204, and the exhaust hose 306 may be referred to as the exhaust flow path 308. As used herein, "back pressure" may refer to the pressure within the cryosurgical probe 102 due to the effects of the exhaust flow path 308. For example, increasing the cryogenic fluid 302 flow rate through the exhaust flow path 308 and/or throttling exhaust valve 204 may increase the back pressure. Similarly, lowering the cryogenic fluid 302 flow rate through the exhaust path 308 and/or fully opening the exhaust valve 204 may reduce the back pressure.

The cryosurgical control unit 200 may be configured to control cooling and/or heating of the cryosurgical probe 102, such as by selectively supplying cryogenic fluid 302 to the cryosurgical probe 102 via the inlet conduit 104. To supply the cryogenic fluid 302 to the cryosurgical probe 102 via the inlet conduit 104, the cryogenic control unit 200 may at least partially open the inlet valve 202, which may allow cryogenic fluid 302 to flow to from the cryogenic fluid source 300, through the cryogenic fluid supply line 304, through the inlet valve 202, through the inlet conduit 104, and to cryogenic probe 102.

The cryosurgical control unit 200 may be configured to control cooling and/or heating of the cryosurgical probe 102, such as by selectively permitting cryogenic fluid 302 to flow from the cryosurgical probe 102 via the exhaust conduit 106. To permit cryogenic fluid 302 to flow from the cryogenic probe 102 via the exhaust conduit 106, cryogenic control unit 200 may at least partially open the exhaust valve 204, which may allow cryogenic fluid 302 to flow from the cryogenic probe 102, through the exhaust conduit 106, through the exhaust valve 204, and through the exhaust hose 306.

In some example embodiments, the cryogenic fluid source 300 may include a pressurized tank 310 containing liquid 312 and gas 314 phases of the cryogenic fluid 302. In some example embodiments, the cryogenic control unit 200 may be configured to receive the cryogenic fluid 302 as a gas. In some example embodiments, the cryogenic fluid 302 may include nitrous oxide and/or carbon dioxide.

In some example embodiments, the cryogenic surgical system 100 may include a heater in thermal communication with the cryogenic fluid 302 in the tank 310. For example, a heater band 111 may be removably disposed at least partially around and/or may be thermally coupled to an exterior wall 316 of the tank 310. In some example embodiments, the heater band 111 may be disposed on a lower portion 318 of the exterior wall 316 of the tank 310. The cryogenic surgical system 100 may include a pressure sensor 112 arranged to measure the pressure of the fluid 302 coming from or within the tank. For example, the pressure sensor 112 may be disposed within the cryogenic control unit 200 and/or may be fluidically coupled to the cryogenic fluid supply line 304. During operation of the heater band 111, the heat output of the heater band 111 may be varied to maintain the pressure of the cryogenic fluid 302 in the tank 310 within a pressure setpoint range, such as by cycling electrical power to the heater band on and off.

The cryogenic surgical system 100 may include a temperature sensor 114 arranged to measure a temperature associated with the tank 310, such as the temperature of the exterior wall 316 of the tank 310. In some example embodiments, the temperature sensor 114 may be disposed on the heater band 111 proximate an upper end 116 of the heater band 111.

In some example embodiments, the cryogenic surgical system 100 may be configured to display one or more indicia associated with the liquid level 320 in the tank 310. As used herein, "displaying an indicium" may refer to providing any audible indication (e.g., beep and/or tone), visual indication (e.g., numerical and/or graphical indication), and/or tactile indication (e.g., shaking and/or vibration), which may be understood to convey information, such as information about the liquid level 320 in the tank 310. For example, the cryogenic control unit 200 may include a graphical indicator 206 configured to visually display one or more indicia associated with the liquid level 320 in the tank 310. In some other example embodiments, indicators may include sound-emitting devices (e.g., speakers, buzzers, beepers, etc.) and/or movement-causing devices (e.g., electric motors with unbalanced masses on the driveshafts).

The cryosurgical control unit 200 may include a processor 208 and/or a data storage device 210, which may be operatively coupled to each other and/or to other components of the cryogenic surgical system 100 and/or which may be configured to control various functions and operations of the cryogenic surgical system 100, such as those described in the present disclosure. For example, the processor 208 and/or the data storage device 210 may be operatively coupled to receive information from, send information to, and/or direct operation of the temperature sensor 110 of the cryosurgical probe 102, inlet valve 202, exhaust valve 204, heater band 111, pressure sensor 112, temperature sensor 114, and/or graphical indicator 206. The cryosurgical control unit 200 may also include an actuator 230 communicatively coupled to the processor 208. The actuator may be configured to be manually actuated when a tank 310 replacement occurs. By way of example, when the actuator 230 is actuated, the processor 208 receives a signal indicative of first discrete liquid level 212 (see FIG. 2) and causes the processor 208 to store and indication of the first discrete liquid level in the data storage device 210.

Figure 2:
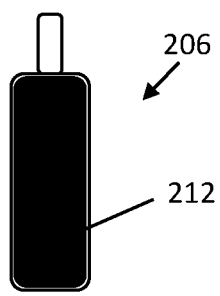
FIG. 2 is a detailed view of an example graphical indicator visually displaying an indicium associated with a first discrete liquid level.
Figure 3:
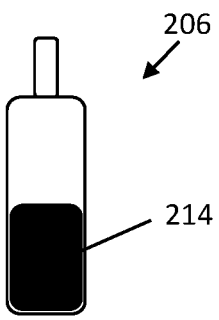
FIG. 3 is a detailed view of the example graphical indicator of FIG. 2 visually displaying an indicium associated with a second discrete liquid level.
Figure 4:
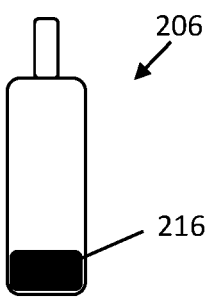
FIG. 4 is a detailed view of the example graphical indicator of FIG. 2 visually displaying an indicium associated with a third discrete liquid level.

FIGS. 2-4 are detailed views of the example graphical indicator 206 of the cryogenic control unit 200, according to at least some aspects of the present disclosure. The graphical indicator 206 may be configured to visually display an indicium associated with a first discrete liquid level 212 (FIG. 2), an indicium associated with a second discrete liquid level 214 (FIG. 3), and/or an indicium associated with a third discrete liquid level 216 (FIG. 4). Referring to FIGS. 1-4, the indicium associated with the first discrete liquid level 212 may correspond to a relatively higher liquid level 322, the indicium associated with the second discrete liquid level 214 may correspond to an intermediate liquid level 324, and/or the indicium associated with the third liquid level 216 may correspond to a relatively lower liquid level 326 in the tank.

In general, any indicia associated with any liquid levels may include part or all of at least some other indicia. For example, in embodiments including bar-graph type displays, one or more of the indicia corresponding to an emptier level may be included in one or more of the indicia corresponding to a fuller level. For example, in graphical indicator 206, the indicium associated with the second discrete level 214 may include a single bar extending approximately half way up, or it may include two or more bars, such that the bar shown as the indicium associated with the third liquid level 216 on the bottom and a second bar above and extending to approximately half way up. Similarly, the indicium associated with the first discrete liquid level 212 may include the indicium associated with the third liquid level 216, a second bar extending to approximately half way up, and/or a third bar extending substantially to the top. As another example, if the indicia include audible beeps, the indicium associated with the third discrete liquid level (e.g., three beeps) may include the indicium associated with the second liquid level (e.g., two beeps), and the indicium associated with the first liquid level (e.g., one beep). More generally, the indicium associated with the first discrete liquid level, the indicium associated with a second discrete liquid level, and/or the indicium associated with a third discrete liquid level are to be considered in their entireties as presented to a user, and the scope of the present disclosure is not limited by the particular format or inclusion of some indicia as elements of another indicium.

Figure 5:
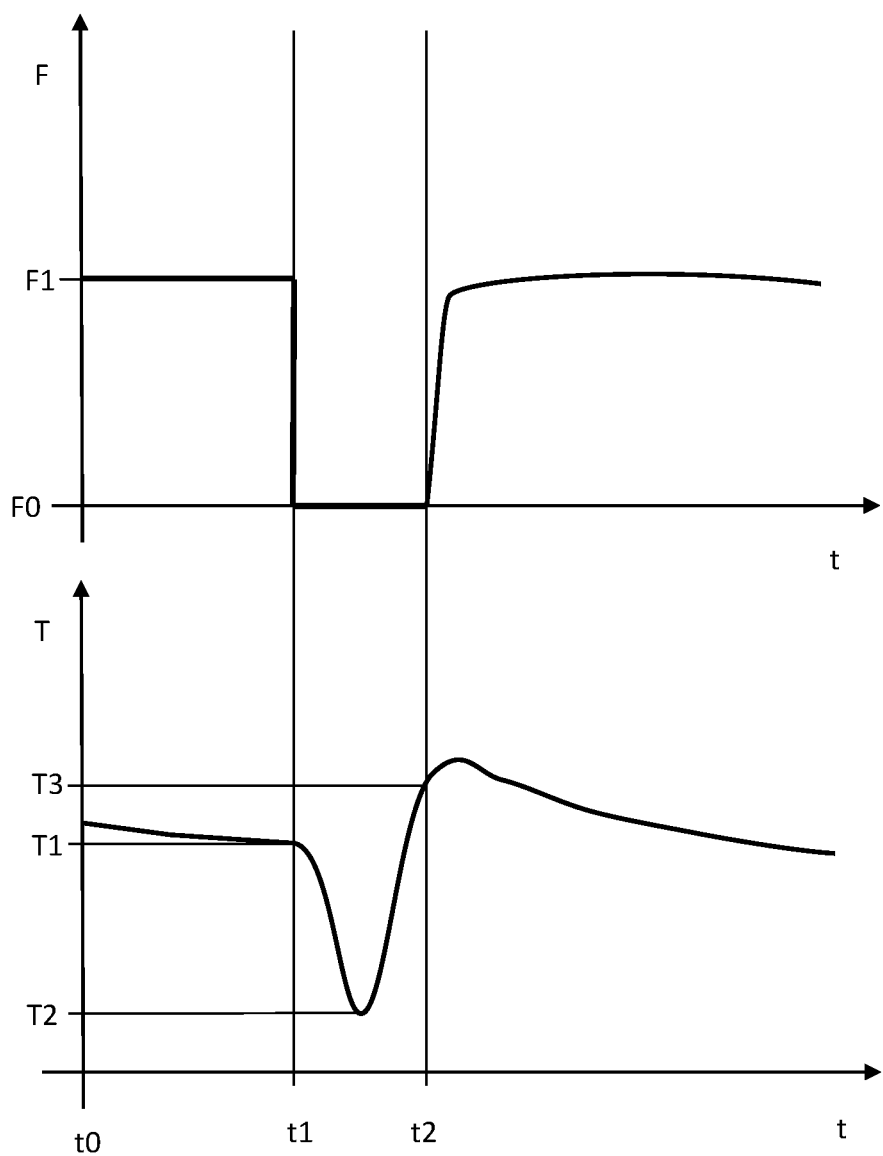
FIG. 5 is a plot of an example cryogenic fluid flow rate and an example cryosurgical probe temperature versus time.

FIG. 5 is a plot of an example cryogenic fluid flow rate (on the axis labeled "F") and an example cryosurgical probe temperature (on the axis labeled "T") versus time (on the axes labeled "t"), according to at least some aspects of the present disclosure. Generally, FIG. 5 illustrates an example temperature response of the cryosurgical probe 102 when cryosurgical control unit 200 controls cooling of the cryosurgical probe 102 by selectively supplying cryogenic fluid 302 to the cryosurgical probe 102 by controlling inlet valve 202.

In this example, the cryosurgical fluid 302 may include nitrous oxide, which may be supplied to the cryosurgical control unit 200 and to the cryosurgical probe 102 as gas. At least some of the gaseous nitrous oxide flowing through the orifice 108 may liquefy due the Joule-Thomson effect. Accordingly, at least some of the cooling effect in the cryosurgical probe 102 may be due to boiling of the liquified nitrous oxide in the cryosurgical probe 102.

Further, in this example, the exhaust valve 204 remains fully open throughout the time shown on the plots. Accordingly, the exhaust flow path 308 for the cryogenic fluid 302 leaving the cryosurgical probe 102 remains substantially the same throughout the time shown on the plots.

At time t0, the cryogenic fluid 302 is flowing to the cryosurgical probe 102 at flow rate F1. For example, flow rate F1 may be approximately the steady state flow rate when the inlet valve 202 is fully open. Temperature T1 may be a first setpoint temperature at which the cryosurgical control unit 200 is configured to shut the inlet valve 202.

When the cryosurgical probe 102 temperature reaches first setpoint temperature T1 at time t1, the cryosurgical control unit 200 may fully shut the inlet valve 202. Accordingly, the cryogenic fluid 302 flow rate drops to flow rate F0, which may be substantially zero flow. With no inlet flow to the cryosurgical probe 102, the exhaust flow rate may drop, which may result in a lower back pressure in the exhaust flow path 308. The lower back pressure may result in a lower pressure in the cryosurgical probe 102, which may allow the cryogenic fluid 302 therein to boil at a lower temperature. Accordingly, a downward temperature transient may occur as shown between time t1 and time t2. The lowest cryosurgical probe 102 temperature reached is temperature T2, which may be lower than the first setpoint temperature T1. This downward temperature transient and/or temperature T2 lower than the first setpoint temperature T1 may facilitate formation of a larger ice ball 105 and/or further cooling of the ice ball 105 and/or target tissue 103.

Eventually, sufficient cryosurgical fluid 302 in the cryosurgical probe 102 may boil and exit via the exhaust path 308 to allow the cryosurgical probe 102 to warm, such as by heating from its surroundings. During this transient, while the cryosurgical probe 102 is cooled to a temperature T2 that is colder than the first setpoint temperature T1, the inlet valve 202 may remain fully shut.

At time t2, the cryosurgical probe 102 has reached a second setpoint temperature T3. Second setpoint temperature T3 may be the temperature at which cryosurgical control unit 200 is configured to open the inlet valve 202. When the cryosurgical control unit 200 fully opens the inlet valve 202, the cryogenic fluid 302 flow rate may rise to and maintain flow rate F1. Restoring the flow of the cryogenic fluid 302 to the cryosurgical probe 102 may cool the cryosurgical probe 102, reducing its temperature.

In some example embodiments, the second setpoint temperature T3 may be warmer than the first setpoint temperature T1. Generally, the back pressure between time t0 and time t1 may be greater than the back pressure between time t1 and time t2.

The present disclosure contemplates that the amount of cryogenic fluid 302 in the tank 310 could be estimated by weighing the tank 310 and subtracting the weight of the empty tank 310. The present disclosure contemplates that this approach, however, would typically require the cryogenic surgical system 100 to include additional instrumentation, such as a load cell configured to weigh the tank 310. Moreover, attempting to ascertain the amount of cryogenic fluid 302 in the tank 310 by weight relies on knowing the weight of the empty tank 310 and that the scale measuring the weight is accurate—both of which may be unknown or inaccurate.

Figure 6:
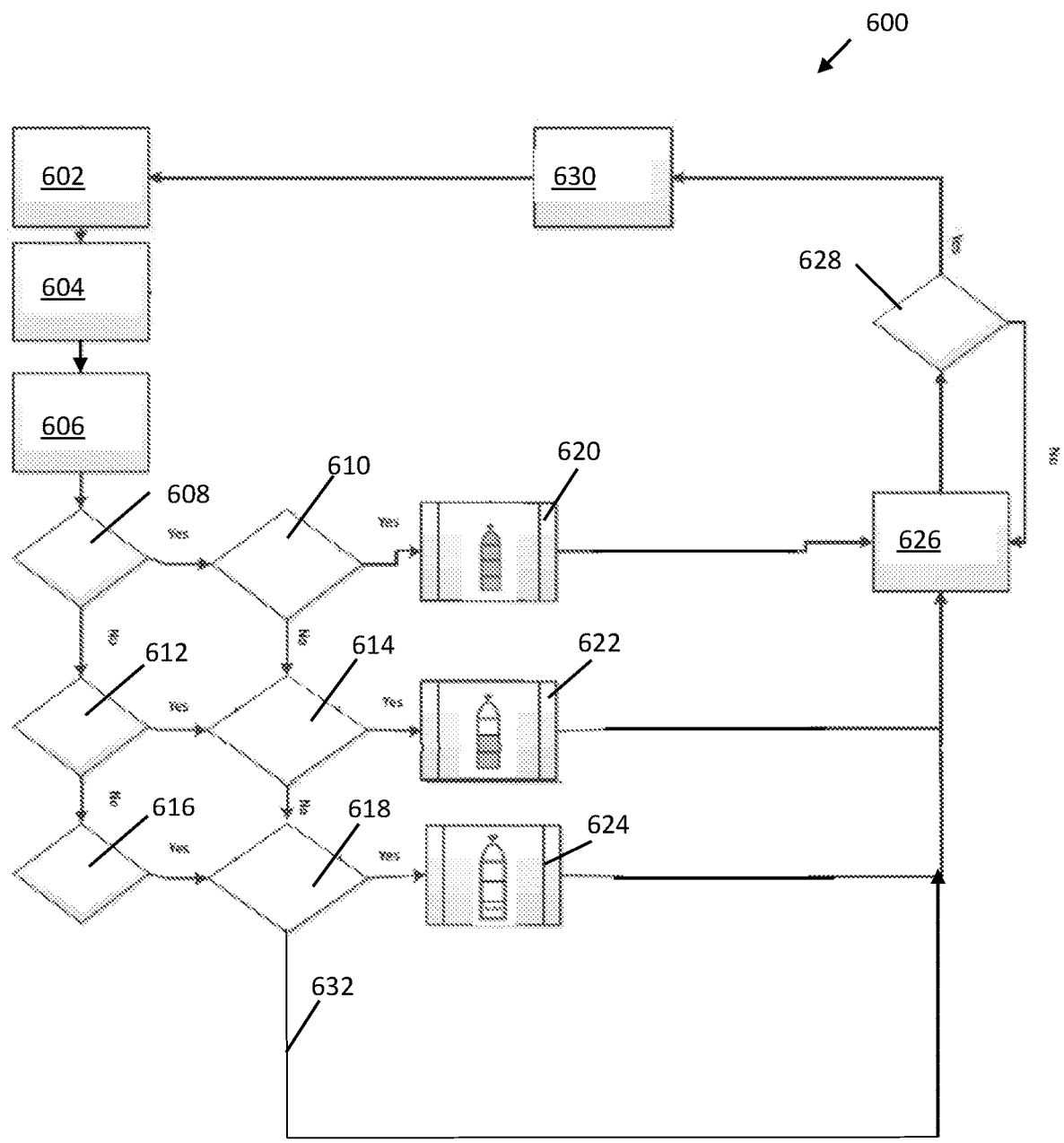
FIG. 6 is a flow diagram of an example method of indicating a liquid level in a tank; all in accordance with at least some aspects of the present disclosure.

Some example cryogenic surgical systems 100 may be configured to indicate the liquid level 320 in the tank 310 based on the pressure of the cryogenic fluid 302 in the tank 310 and the temperature of the exterior wall 316 of the tank 310, such as when the heater band 111 is operating to maintain the pressure of the cryogenic fluid 302 in the tank 310 within the pressure setpoint range. FIG. 6 is a flow diagram of an example method 600 of indicating the liquid level 320 in the tank 310, according to at least some aspects of the present disclosure. In some example embodiments, the method 600 may be utilized in connection with heating the tank 310 using the heater band 111.

The method 600 may begin with operation 602, which may include measuring the pressure of the fluid 302 in the tank 310. It should be noted that, by way of example, the method 600 may be reinitialized upon actuating the actuator 230 indicating a tank 310 replacement, and/or may be reinitialized periodically based upon a predetermined timing such as, without limitation, every thirty seconds, every minute, every two minutes, and every five minutes. Operation 602 may be followed by operation 604, which may include measuring the temperature of the exterior wall 316 of the tank 310. Operation 604 may be followed by operation 606, which may include determining whether an immediately previously displayed indicium was the indicium associated with the first discrete liquid level 212, the indicium associated with the second discrete liquid level 214, or the indicium associated with the third discrete liquid level 216. Operation 606 may be followed by operations 608, 610, 612, 614, 616, and/or 618, which may include determining, in sequence, which sets of criteria are satisfied and, upon determining that the particular set of criteria is satisfied, displaying the indicium associated with the liquid level 320 in the tank 310 that is associated with that particular set of criteria.

Operation 608 may include determining whether the immediately previously displayed indicium was the indicium associated with the first discrete liquid level 212. This operation 608 may include accessing the data storage device 210 to determine what liquid level is currently saved in memory. If the liquid level saved in the data storage device 210 matches the liquid level displayed on the graphical indicator 206, the method 600 may proceed to operation 610. If the liquid level saved in the data storage device 210 does not match the liquid level displayed on the graphical indicator 206, the method 600 may proceed to operation 612.

Operation 610 may include determining whether the pressure of the fluid 302 in the tank 310 is greater than a first threshold pressure and whether the temperature of the exterior wall 316 is less than a first threshold temperature. If the pressure of the fluid 302 in the tank 310 is greater than a first threshold pressure and the temperature of the exterior wall 316 is less than a first threshold temperature, the method 600 may proceed to operation 620. If at least one of (1) the pressure of the fluid 302 in the tank is less than a first threshold pressure and (2) the temperature of the exterior wall 316 is greater than a first threshold temperature, the method 600 may proceed to operation 614.

Operation 620 may include displaying the indicium associated with the first discrete liquid level 212 and updating the data storage device 210 to indicate the first discrete liquid level 212 is being displayed. Following operation 620, the method may proceed to operation 626.

Operation 612 may include determining whether the immediately previously displayed indicium was the indicium associated with the second discrete liquid level 214 by comparing the data storage device 210 stored liquid level with the liquid level displayed on the graphical indicator 206. If the liquid level saved in the data storage device 210 matches the liquid level displayed on the graphical indicator 206 (i.e., the second discrete liquid level 214), then the method 600 may proceed to operation 614. If the liquid level saved in the data storage device 210 does not match the liquid level displayed on the graphical indicator 206, then the method 600 may proceed to operation 616.

Operation 614 may include determining whether the pressure of the fluid 302 in the tank 310 is greater than the second threshold pressure and whether the temperature of the exterior wall 316 is less than the second threshold temperature. If the pressure of the fluid 302 in the tank 310 is greater than the second threshold pressure and the temperature of the exterior wall 316 is less than the second threshold temperature, the method 600 may proceed to operation 622. If at least one of (1) the pressure of the fluid 302 in the tank 310 is less than the second threshold pressure and (2) the temperature of the exterior wall 316 is greater than the second threshold temperature, the method 600 may proceed to operation 618.

Operation 622 may include displaying the indicium associated with the second discrete liquid level 214 and updating the data storage device 210 to indicate the second discrete liquid level 214 is being displayed. Following operation 622, the method may proceed to operation 626.

Operation 616 may include determining whether the immediately previously displayed indicium was the indicium associated with the third discrete liquid level 216 (or some other predetermined liquid level besides the first and second discrete liquid levels 212, 214). If the liquid level was not one of the first discrete liquid level 212 or the second discrete liquid level 214, by reference to the liquid level saved in the data storage device 210, the method may proceed to operation 618.

Operation 618 may include determining whether the pressure of the fluid 302 in the tank 310 is less than the third threshold pressure and the temperature of the exterior wall 216 is greater than or equal to the third threshold temperature. If the pressure of the fluid 302 in the tank 310 is less than the third threshold pressure and the temperature of the exterior wall is greater than the third threshold temperature, the method 600 may proceed to operation 624. If at least one of (1) the pressure of the fluid 302 in the tank 310 is greater than the third threshold pressure and (2) the temperature of the exterior wall 316 is less than the third threshold temperature, the method 600 may proceed to operation 632 that includes maintaining the instant/current indicium displayed via operation 620, 622, or 624 and proceed to operation 626.

Operation 624 may include displaying the indicium associated with the third discrete liquid level 216. Following operation 624, the method may proceed to operation 626.

Operations 626, 628, and 630 may function as a timer, which may be configured to periodically reinitiate method 600 at operation 602. Operation 626 may increment a timing counter. Operation 628 may determine whether the timing counter has reached a timing threshold (e.g., 30 seconds). If no, the method 600 may return to operation 626, which may again increment the timing counter. Once the timing counter has reached the timing threshold, operation 630 may follow operation 628. Operation 630 may reset the timing counter incremented in operation 626 (e.g., to zero). The method 600 may return to operation 602 following operation 630. In the next cycle, the indicium indicated in the previous cycle in operation 620, operation 622, or operation 624 may be used as the immediately previously displayed indicium in operation 608, operation 612, and/or operation 616.

In some example embodiments, method 600 may take into account whether the tank 310 is a full replacement tank 310. For example, in the first cycle through method 600 with a full replacement tank, method 600 may consider the immediately previously displayed indicium to be the indicium associated with the first discrete liquid level 212.

In some example embodiments, the first threshold pressure and the second threshold pressure may be substantially the same. In some example embodiments the third threshold pressure may be higher than at least one of the first threshold pressure and the second threshold pressure. In some example embodiments, the third threshold temperature may be higher than the first threshold temperature and the second threshold temperature. In some example embodiments, the liquid level may be displayed based on only the parameters explicitly described above in connection with the method 600 (e.g., the pressure of the fluid in the tank and the temperature of the exterior wall of the tank), and not utilizing additional parameters such as the differential pressure between two heights in the tank, the tank weight, the temperatures at multiple locations on the tank wall, etc. In some example embodiments, the method 600 may include consideration of any of these additional parameters and/or other additional parameters.

By way of example, the first threshold pressure may be greater than or equal to 700 psi, while the first threshold temperature may be between 20 C to 30 C and, optionally less than 27 C. By way of further example, the second threshold pressure may be greater than or equal to 700 psi, while the second threshold temperature may be between 21 C to 40 C and, optionally less than 31 C, and even less than 29 C. By way of still further example, the third threshold pressure may be less than or equal to 770 psi, optionally between 770 psi and 600 psi, while the third threshold temperature may be greater than the second threshold temperature, and optionally greater than or equal to 31 C.

Following from the above description and invention summaries, it should be apparent to those of ordinary skill in the art that, while the methods and apparatuses herein described constitute example embodiments according to the present disclosure, it is to be understood that the scope of the disclosure contained herein is not limited to the above precise embodiments and that changes may be made without departing from the scope as defined by the following claims. Likewise, it is to be understood that it is not necessary to meet any or all of the identified advantages or objects disclosed herein in order to fall within the scope of the claims, since inherent and/or unforeseen advantages may exist even though they may not have been explicitly discussed herein.

What is claimed is:

1. A cryogenic surgical system, comprising:
   a cryosurgical probe fluidically interposing an inlet conduit arranged to supply a cryogenic fluid to the cryosurgical probe and an exhaust conduit arranged to direct the cryogenic fluid away from the cryosurgical probe; and
   a cryosurgical control unit capable of receiving the cryogenic fluid from a cryogenic fluid source, the cryosurgical control unit comprising an inlet valve fluidically coupled to the inlet conduit and configured to selectively supply the cryogenic fluid to the cryosurgical probe via the inlet conduit and an exhaust valve fluidically coupled to the exhaust conduit and configured to selectively permit cryogenic fluid to flow from the exhaust conduit
   wherein the cryosurgical control unit includes at least one of a processor and a data storage device configured to control cooling of the cryosurgical probe to a temperature lower than a first setpoint temperature by (1) cooling the cryosurgical probe by directing opening of the inlet valve to supply the cryogenic fluid to the cryosurgical probe, (2) directing shutting of the inlet valve when a temperature of the cryosurgical probe reaches the first setpoint temperature, and (3) directing the inlet valve remains shut while the cryosurgical probe temperature is less than the first setpoint temperature.

2. The system of claim 1, wherein at least one of the processor and the data storage device is configured to direct opening of the inlet valve to supply the cryogenic fluid to the cryosurgical probe when the temperature of the cryosurgical probe reaches a second setpoint temperature, after the inlet valve remains shut while the cryosurgical probe temperature is less than the first setpoint temperature.

3. The system of claim 2, wherein the second setpoint temperature is higher than the first setpoint temperature.

4. The system of claim 1, wherein at least one of the processor and the data storage device is configured to control cooling of the cryosurgical probe to a temperature less than the first setpoint temperature by (1) cooling the cryosurgical probe by directing opening of the inlet valve to supply the cryogenic fluid to the cryosurgical probe and directing opening of the exhaust valve to permit the cryogenic fluid to exhaust from the cryogenic probe, (2) directing shutting of the inlet valve and directing the exhaust valve remains open when the temperature of the cryosurgical probe reaches the first setpoint temperature, (3) directing the inlet valve remains shut and directing the exhaust valve remains open while the cryosurgical probe temperature is less than the first setpoint temperature.

5. The system of claim 1,
   wherein the cryosurgical control unit is configured to receive the cryogenic fluid as a gas; and
   wherein the cryosurgical probe includes an orifice capable of liquefying at least a portion of the gas.

6. The system of claim 5, wherein the cryosurgical fluid comprises at least one of gaseous nitrous oxide and gaseous carbon dioxide.

7. A method of operating a cryosurgical probe, the method comprising:
   cooling the cryosurgical probe to a first setpoint temperature by supplying a cryogenic fluid to the cryosurgical probe via an inlet valve;
   shutting the inlet valve when a temperature of the cryosurgical probe reaches the first setpoint temperature; and
   cooling the cryosurgical probe to a temperature lower than the first setpoint temperature while the inlet valve remains shut.

8. The method of claim 7, further comprising, after cooling the cryosurgical probe to the temperature lower than the first setpoint temperature, opening the inlet valve when the temperature of the cryosurgical probe reaches a second setpoint temperature.

9. The method of claim 8, wherein the second setpoint temperature is higher than the first setpoint temperature.

10. The method of claim 7,
    wherein cooling the cryosurgical probe to the first setpoint temperature includes exhausting the cryogenic fluid from the cryosurgical probe via an exhaust valve; and
    wherein a position of the exhaust valve is not changed during cooling the cryosurgical probe to the first setpoint temperature operation, the shutting the inlet valve operation, and cooling the cryosurgical probe to the temperature less than the first setpoint temperature operation.

11. The method of claim 7,
    wherein cooling the cryosurgical probe to the first setpoint temperature comprises operating the cryosurgical probe at a first back pressure; and
    wherein cooling the cryosurgical probe to the temperature less than the first setpoint temperature comprises operating the cryosurgical probe at a second back pressure, the second back pressure being lower than the first back pressure.

12. The method of claim 7, wherein an exhaust flow path for cryogenic fluid leaving the cryosurgical probe is substantially the same in cooling the cryosurgical probe to the first setpoint temperature operation and cooling the cryosurgical probe to the temperature less than the first setpoint temperature operation.

13. The method of claim 7,
    wherein the cryosurgical fluid is supplied to the cryosurgical probe as a gas; and
    wherein cooling the cryosurgical probe to the first setpoint temperature operation comprises liquefying at least a portion of the gas by flowing the gaseous cryogenic fluid through an orifice.

14. The method of claim 13, wherein the cryosurgical fluid comprises at least one of gaseous nitrous oxide and gaseous carbon dioxide.

* * * * *